United States Patent [19]

Marman et al.

[11] Patent Number: 5,053,545
[45] Date of Patent: Oct. 1, 1991

[54] METHOD OF PREPARING AMINO ALCOHOLS

[75] Inventors: Thomas H. Marman, Palatine; Vincent Nocito, Buffalo Grove, both of Ill.

[73] Assignee: Angus Chemical Company, Northbrook, Ill.

[21] Appl. No.: 564,540

[22] Filed: Aug. 7, 1990

Related U.S. Application Data

[63] Continuation-in-part of Ser. No. 279,527, Dec. 2, 1988, abandoned.

[51] Int. Cl.$^5$ ............................................. C07C 209/34
[52] U.S. Cl. .................................... 564/495; 564/489; 564/494
[58] Field of Search ......................................... 564/495

[56] References Cited

U.S. PATENT DOCUMENTS

| | | | |
|---|---|---|---|
| 2,157,386 | 5/1939 | Johnson | 564/495 |
| 2,538,763 | 1/1951 | Crooks et al. | 564/358 |
| 2,587,572 | 2/1952 | Tryon | 564/495 |
| 3,564,057 | 2/1971 | Tindall | 564/495 |
| 4,221,740 | 9/1980 | Pfeiffer | 564/495 |

FOREIGN PATENT DOCUMENTS 1230428  12/1966  Fed. Rep. of Germany ....... 564/495

OTHER PUBLICATIONS

Iguchi, Y, "A process for the preparation of 2-amino-1,3-poopanectiol", CA 108, 166968v (1988).
Iio, A et a, "Preparation of Aminoalcohols as drug intermediates", CA 112, 98019s (1990).

Primary Examiner—Glennon H. Hollrah
Assistant Examiner—Susan Treanor
Attorney, Agent, or Firm—Leydig, Voit & Mayer

[57] ABSTRACT

A method of preparing an amino alcohol of the formula

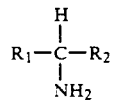

where $R_1$ is H, lower alkyl or $R_2$, $R_2$ is $R_3$CHOH in which $R_3$ is H, alkyl or aryl. $R_3$ preferably is hydrogen, lower alkyl or monocyclic aryl such as phenyl. The inventive method involves the reaction of halonitroalcohol with hydrogen in the presence of methanol, a suitable buffering agent such as ammonia, and a hydrogenation catalyst to form amino alcohol salt, neutralizing the amino alcohol salt, and recovering the resultant amino alcohol.

9 Claims, No Drawings

METHOD OF PREPARING AMINO ALCOHOLS

This is a continuation-in-part of application Ser. No. 279,527 filed Dec. 2, 1988 now abandoned in the name of Thomas H. Marman.

This invention is in the field of chemical synthesis and is directed to a method for the preparation of amino alcohols of the type represented by serinol (2-amino-1,3 propanediol).

BACKGROUND OF THE INVENTION

Among their many uses, amino alcohols are useful in the preparation of radiopaque agents. Previous methods of preparation, however, have resulted in products which contain a number of by-products which are sometimes difficult to remove from the desired amino alcohols, thereby rendering the products not entirely suitable for such uses.

A method of preparing amino alcohols is described in U.S. Pat. No. 2,157,386. The disclosed process comprises hydrogenating aliphatic nitroalcohol in the liquid phase, e.g., by using an inert solvent for the nitroalcohol, in the presence of a nickel hydrogenation catalyst at a temperature from about 15° C. to about 165° C. In one example, 2-nitro-1-butanol was hydrogenated in the presence of ethanol and nickel catalyst at a pressure of 600 pounds for 8 hours and at a temperature of 25°-30° C. Conversion of the nitrobutanol to amino compounds was reported to be over 92%, but conversion to 2-amino-1-butanol was reported to be only 74.5%.

U.S. Pat. No. 2,587,572 discloses a process for the preparation of amino alcohol whereby nitroalcohol is slowly introduced into a reaction vessel containing hydrogen, an inert solvent, and a hydrogenation catalyst at a pressure of 20-200 psi and temperature of 40°-100° C., such that hydrogenation is completed substantially instantaneously as the nitroalcohol enters the reaction zone. The examples utilize methanol as the solvent and nickel catalyst. The yields reported in the examples were 69% and 95.8%, and the process was generally said to provide for yields of 80-90%.

U.S. Pat. No. 3,564,057 discloses a process for the production of primary alkanolamines by the reduction of the corresponding nitroalkanol, wherein the ratio of secondary to primary alkanolamines is reportedly reduced by effecting the reduction in the presence of ammonia or a soluble primary or secondary aliphatic amine. The examples illustrate the reduction being effected with hydrogen at elevated pressure and temperature and in the presence of methanol, formaldehyde, Raney nickel catalyst, and the soluble amine. No specific yields or purity levels, however, are reported.

U.S. Pat. No. 4,221,740 discloses a process for the preparation of 2-amino-1,3-propanediol by catalytically hydrogenating the sodium salt of 2-nitro-1,3-propanediol. The examples illustrate this reaction taking place in methanol with ammonium chloride as a neutralizing agent for the produced sodium hydroxide and Raney nickel as the catalyst at 70 atmospheres pressure and at room temperature. Favorable results are shown only when low temperature (10°-27° C.) is employed, which is a quite impractical temperature to maintain under production conditions. Yields as high as 82% are reported. The reaction employs sufficient formaldehyde to form an undesirable amount of tris-nitro, an impurity that affects yield of the desired product.

U.S. Pat. No. 4,448,999 also discloses a process for the preparation of 2-amino-1,3-propanediol. It states that the process shown in 4,221,740 was not reproducible and produced resinous by products and unstable materials which made it impossible to recover serinol. The disclosed process involves catalytically hydrogenating an alkali salt of 2-nitro-1,3-propanediol in the presence of inert solvents and a buffered acid under pressure of 1-98 bar hydrogen, while maintaining the temperature in the narrow range of 50°-80° C. by use of a cooling device during the reaction, i.e., for a period of time of from 15 to 300 minutes. The examples utilize the sodium salt of 2-nitro-1,3-propanediol, methanol as the inert solvent, ammonium chloride as the buffered acid, and a catalyst comprising 5% Pd/C, 50% water-moist. Reported yields ranged from 74% to more than 95%. The reaction employs sufficient formaldehyde to form an indesirable amount of tris-nitro, an impurity that affects yield of the desired product.

BRIEF SUMMARY OF THE INVENTION

It is an object of the present invention to provide an improved method of preparing amino alcohols.

It is a further object of this invention to provide a method of preparing amino alcohols of high purity.

Yet another object of this invention is to provide a process for the preparation of amino alcohols which can be operated as either a batch or semi-continuous process.

These and other objects and advantages of this invention, as well as additional inventive features, will become apparent from the description which follows.

Amino alcohols are prepared in accordance with the present invention by hydrogenating a halonitroalcohol in the presence of methanol, a suitable buffering agent, and a hydrogenation catalyst, neutralizing the resulting amino alcohol salt, and recovering the resultant amino alcohol.

DETAILED DESCRIPTION OF THE INVENTION

While the invention will be described in connection with certain preferred embodiments, it is not intended to limit the invention to the particular embodiments. On the contrary, it is intended to cover all alternatives, modifications, and equivalent processes as may be included within the spirit and scope of the invention as defined by the appended claims.

The present invention constitutes a method of preparing amino alcohols of the formula

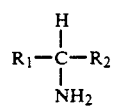

$R_1$ is H, lower alkyl or $R_2$, $R_2$ is $R_3$CHOH in which $R_3$ is H, alkyl or aryl. $R_3$ preferably is hydrogen, lower alkyl or monocyclic aryl such as phenyl. The inventive method involves the reaction of halonitroalcohol with hydrogen in the presence of methanol, a suitable buffering agent such as ammonia, and a hydrogenation catalyst to form amino alcohol salt, neutralizing the amino alcohol salt, and recovering the resultant amino alcohol.

Among the advantages of this process are; (1) the chloropol or bronopol intermediate is quite stable and can be held in a dry state for long periods of time; (2) chloropol is fed to the reactor as a solution and no line blockage will occur; (3) hydrogen can be fed at any convenient rate; (4) the initial product is serinol hydrochloride which can be washed and recrystallized to high purity in good yield.

The halonitroalcohol may be prepared by any procedure. Generally halonitroalkane is initially prepared by a suitable procedure, such as those disclosed in U.S. Pat. Nos. 2,309,806 and 3,096,378, but preferably by the following procedure which is the subject of copending U.S. application Ser. No. 07/529,747 filed of even date herewith and whose disclosure is incorporated herein by reference.

The preferred method involves the reaction of a nitronate salt, with a halogen to form the monohalogenated nitroalkane which is subsequently recovered from the reaction mixture.

The nitronate salt is prepared by reacting essentially equal molar quantities of an alkali metal hydroxide and a nitroalkane. The reaction may take place in any suitable vessel equipped with an agitator and cooling jacket or may be performed in a continuous reactor consisting of a tube containing a static mixer. The reaction takes place at low temperature, below about 40° C. and when in a batch operation at low temperature, e.g., 0° C. ±10° C., and preferably in an aqueous medium in which an aqueous solution of the nitroalkane is mixed with an aqueous solution of the alkali metal hydroxide, resulting in an aqueous solution of the nitronate salt. Other solvents can also be used. The preferred alkali metal hydroxide is sodium hydroxide, but other alkali metal hydroxides can be utilized in the practice of the present invention.

The nitronate salt thus formed is promptly mixed with a halogen in equal molar quantities. Again, the reaction may take place in any suitable vessel as described in the preceding paragraph. Preferably, an aqueous nitronate salt solution is charged into a reactor containing a solution of the halogen. Cooling is supplied to maintain the vessel at low temperature, as recited in the previous paragraph, with agitation. If a continuous system is desired, anhydrous halogen or a halogen solution can be fed into a tube reactor equipped with a static mixer simultaneously and in equal molar quantity with the nitronate salt solution. The process is preferably operated in an aqueous system, although other solvent systems can also be utilized. For example, if the halogen is not sufficiently water-soluble, a different, more suitable, solvent for the halogen may be used, such as methylene chloride.

Immediately following formation of the monohalogenated nitroalkane, the solution is treated with a compound to destroy any unreacted halogen in the reaction mixture. The compound employed to destroy any unreacted halogen is preferably sodium bisulfite and is preferably added to the reaction mixture in the form of a saturated solution.

The resulting monohalogenated nitroalkane is recovered from the reaction mixture, preferably by distillation of a solvent azeotrope of the desired product and separation of the bottom product layer by decantation from a suitable distillation trap. The monohalogenated nitroalkane produced by this process will be on the order of 90-95% pure.

The halonitroalcohol may then be prepared from the halonitroalkane by any suitable procedure, such as the procedures disclosed in U.S. Pat. Nos. 3,658,921 and 3,711,561, although the procedure set forth below, which is the subject of U.S. Pat. No. 4,922,030 is preferred.

Preparation of the desired halonitroalcohol is accomplished by reacting the halonitroalkane with a substantially nonaqueous aldehyde solution in the presence of an alkaline catalyst. While any suitable aldehyde may be used, formaldehyde is the commercially preferred aldehyde. Any suitable solvent or mixture of solvents may be used for the aldehyde, so long as the solvent is substantially nonaqueous. Methanol is the preferred solvent. Either inorganic or organic catalysts may be used. Suitable catalysts include sodium carbonate, sodium bicarbonate, sodium hydroxide, potassium hydroxide, triethyl amine, and n-butyl amine. Primary and secondary amines such as trishydroxymethyl amino methane and morpholine, however, do not function well as the catalyst. Sodium hydroxide is the preferred catalyst. The reaction is exothermic, and the temperature is controlled to maintain the reaction temperature between about 20°-60° C.

Following completion of the above reaction, the resulting halonitroalcohol can be recovered by any suitable means, preferably by lowering the temperature of the reaction material to about 25° C. in an agitated crystallizer with filtration of the crystals. Additional crops of crystals can be obtained in this manner by further lowering the temperature and concentrating the mother liquor. The recovered halonitroalcohol has a purity on the order of 95-99%.

Preparation of the desired amino alcohol is accomplished by catalytically hydrogenating the halonitroalcohol in the presence of methanol and ammonia. Any suitable hydrogenation catalyst such as palladium or activated nickel may be used. Moreover, while any suitable reaction vessel and reactant introduction means may be used to allow for the reaction to take place at elevated pressure and temperature, preferably the halonitroalcohol is dissolved in methanol and the solution added incrementally to an autoclave into which methanol, ammonia, and Raney nickel catalyst have been previously charged. The autoclave is pressured to about 80 psi or higher with hydrogen and maintained at a temperature of about 55° C. to about 80° C. during the addition of the halonitroalcohol/methanol solution. This reaction results in the preparation of the acid salt of an amino alcohol.

The said acid salt is subsequently recovered, preferably by crystallization which removes high molecular weight impurities and color bodies. The resulting crystalline product is then treated with an alkaline material to neutralize the acid salt. While any suitable alkaline material and technique for treating the amino alcohol-acid salt may be used, preferably the amino alcohol-acid salt is dissolved in water to which sodium hydroxide is then added. The alkali treatment results in the preparation of a solution of amino alcohol, which can be recovered by any suitable means, preferably by treating the solution with isopropanol or isobutanol to allow azeotropic removal of water and filtration of the neutralizing salt, followed by distillation to obtain high purity amino alcohol.

The following examples further illustrate the present invention but, of course, should not be construed as in any way limiting its scope.

EXAMPLE 1

This example sets forth a procedure for the preparation of monochloronitromethane.

The apparatus used to prepare monochloronitromethane included three reactors: a nitronate reactor, a chlorination reactor, and a distillation reactor. The nitronate reactor was a 500 ml, round-bottom flask equipped with a thermometer, agitator, two feed reservoirs and pumps, and a nitrogen purge line. The chlorination reactor was a 12 liter, round-bottom flask equipped with a dry ice reflux condenser, inlets for chlorine and nitronate, an agitator, and a scrubber (10% NaOH/10% NaHSO$_3$). The distillation reactor was a 12 liter, round-bottom flask equipped with a thermometer, agitator, 1.5 feet Vigreux column, a Dean-Stark trap, and a scrubber (10% NaOH/10% NaHSO$_3$).

The following procedure was followed in preparing the monochloronitromethane. 6,100 grams of a 10 percent aqueous nitromethane (10 moles) solution was charged to the feed tank of the nitronate reactor, and 2,000 grams of a 20 percent sodium hydroxide (10 moles) solution was charged to the second feed tank of the nitronate reactor. The overflow nitronate reactor (500 ml) was charged with 150 ml of DI water and then cooled to 0° C. with a dry ice-acetone bath. The dip pipe of the nitronate reactor was adjusted to give a residence time of three minutes at a feed rate of 53.3 cc per minute. The chlorination reactor was charged with one liter of methylene chloride and then cooled to −5° C. with a dry ice-acetone bath. The agitator was then started. Chlorine was sparged into the methylene chloride until a gentle reflux of liquid chlorine was apparent in the dry ice reflux condenser. At that time, the flow of nitrogen was started to the nitronate reactor (20 cc/minute). After two minutes, the nitromethane feed pump was started (41.5 ml/minute) along with the sodium hydroxide feed pump (11.8 ml/minute). The temperature in the nitronate reactor was continuously monitored and maintained at 0°-5° C.

The flow of chlorine to the chlorination reactor was then started (feed rate: 8.5 grams/minute for the first 40 minutes, 5.95 grams/minute for the next 30 minutes, 2.55 grams/minute for the final 55 minutes). The sodium nitronate solution (yellow) overflowed continuously to the chlorination reactor, and the temperature in the chlorination reactor was maintained at 0°-5° C. A total of 760 grams of chlorine was fed to the reactor (10.7 moles) over the 2.6 hour nitronate feed period.

Upon completion of the feed addition, the nitronate pumps were stopped. The reaction mixture was allowed to warm to 25° C. and then stirred for one hour. The solution was cloudy yellow with a bright yellow organic phase at the bottom.

The entire contents of the reaction flask were transferred to the distillation reactor. The reaction mixture was heated to boiling (atmospheric pressure), and the scrubber was used to remove chlorine evolved during the heating. A forecut was collected up to a head temperature of 91° C. The product cut was collected as the bottom layer of the azeotrope (91°-101° C. head; 94°-104° C. pot).

By following the foregoing procedure, 824 grams of product was recovered containing 88 wt. % monochloronitromethane, 2-3 wt. % dichloronitromethane, 1-2 wt. % trichloronitromethane, and 5-7 wt. % nitromethane. It is believed that the nitromethane in the product could have been removed from the recovered product by increasing the temperature of the forecut to 94° C.

EXAMPLE 2

This example illustrates the preparation of 2-chloro-2-nitro-1,3-propanediol ("chloropol") using chloronitromethane prepared in a manner similar to that used to prepare the chloronitromethane of Example 1.

1,816 grams of methyl formcel (55 percent CH$_2$O, 35 percent MeOH, 10 percent H$_2$O, 33.26 moles CH$_2$O) were charged into a four liter resin kettle, equipped with a thermometer, pH probe and controller, agitator, chloronitromethane feed pump, and NaOH feed pump. The reactor was cooled to 15° C. in an ice water bath, and the agitator was started.

The pH controller was started, and the reaction mixture was adjusted to an initial pH of 10 by metered addition of 50 percent NaOH.

1,543.2 grams of 88 wt. % chloronitromethane prepared in a manner similar to that set forth in Example 1 was charged to the feed tank. The pH controller was set to 8.5, and the chloronitromethane feed pump (25.7 grams/minute) was started. The temperature was allowed to rise to 55° C., with cooling being applied as needed. Care was taken not to allow the pH to drop below 8.5 by addition of NaOH solution as necessary. The chloropol began to crystallize toward the end of the chloronitromethane addition.

The reaction mixture was stirred for 45 minutes at 55° C. upon completion of the chloronitromethane addition. The chloropol solution was then cooled to 35° C., and the pH was quenched to 5.4 with concentrated HCl.

Cooling was continued until the chloropol slurry reached 25° C., whereupon a first crop of chloropol (1,562.8 grams) was collected. The mother liquor was then cooled and concentrated, and a second crop (444.8 grams) and third crop (114.0 grams) of crystals at 10° C. and 0° C., respectively, were collected. Total yield of chloropol was 2,121.6 grams (13.6 moles, 92 percent molar yield) with an average purity of 96 percent.

EXAMPLE 3

This example illustrates the preparation of a solution of 2-amino-1,3-propanediol-acid salt using the chloropol prepared in Example 2.

An autoclave was inerted with nitrogen, and its pressure checked at 150 psi. The autoclave was then vented to atmospheric pressure. 60 grams of Activated Metals (50 percent wet) A5200 Raney nickel catalyst was charged to the autoclave, followed by 600 ml (475 grams) of methanol and 60.82 grams of 28 wt. % ammonia solution (1.0 mole). Following these additions, the agitator in the autoclave was started, and the autoclave was pressurized to 150 psi with hydrogen and heated to 65° C.

162 grams of the chloropol of Example 2 (96 percent pure, 1.0 mole) was dissolved in 500 grams of methanol. This chloropol solution was then incrementally fed to the autoclave over a 30 minute period. The system pressure was maintained at 150 psi, and the temperature was maintained at 65° C. After the complete chloropol solution was added, the feed lines were flushed with 50 ml of fresh methanol, and stirring of the autoclave was continued for two hours. At the end of this period, the autoclave was cooled to room temperature, and the autoclave pressure was reduced to atmospheric pressure by venting the autoclave to the atmosphere.

The reaction solution was filtered through a bed of Celite 545, and the filter pad was washed with 50 ml of methanol.

The filtered autoclave product (blue solution) was concentrated at 60° C. and 30 mm Hg, and approximately 150 grams of green oil was obtained, comprising approximately 78 wt. % 2-amino-1,3-propanediol.HCl of 94 percent purity. The yield was about 91%.

EXAMPLE 4

This example illustrates the purification and subsequent neutralization of the 2-amino-1,3-propanediol-acid salt prepared in Example 3 and recovery of the resulting 2-amino-1,3-propanediol.

163.5 grams of the green oil obtained in Example 3 (containing one mole of 2-amino-1,3-propanediol.HCl) was charged into a 500 ml round bottom flask, equipped with an agitator and thermometer. 80 grams of methanol was then charged to the reaction flask, and the contents were agitated for 10 minutes at 60° C.

A first crop of 2-amino-1,3-propanediol.HCl crystals (75 grams) was collected at room temperature and washed with 32 grams of cold methanol. The washings were combined with the mother liquor.

The mother liquor was concentrated (45° C., 10 mm Hg) and then cooled to 10° C. A second crop of 2-amino-1,3-propanediol.HCl crystals (25 grams) was collected and washed with 20 grams of cold methanol. The washings were combined with the mother liquor.

The mother liquor was again concentrated (45° C., 100 mm Hg) and cooled to 0° C. A third crop of 2-amino-1,3-propanediol.HCl crystals (13.5 grams) was collected. The overall yield of the recrystallization was 89% 2-amino-1,3-propanediol.HCl of 99.3 percent purity. The crystals were faint green in color.

The three crops of 2-amino-1,3-propanediol.HCl crystals (113.5 grams) were combined and dissolved in 170.3 grams of deionized water. 35.6 grams of NaOH pellets were added to the solution in small increments, and the solution temperature was not allowed to rise above 50° C.

The solution was then concentrated (50° C., 20 mm Hg), and 130–140 grams of water was collected.

140 grams of anhydrous isobutanol were charged to the remainder of the solution. The remaining water was azeotroped off at 50° C. and 20 mm Hg using a distillation system equipped with a Vigreux column and a Dean-Stark trap. Salt precipitated during this concentration step. An additional 40 grams of isobutanol were then added to the mixture.

The salt was filtered from the 2-amino-1,3-propanediol using a pressure filter. Approximately 51 grams of salt were recovered.

The 2-amino-1,3-propanediol solution was concentrated, and 35–39 grams of isobutanol were recovered. The remainder of the 2-amino-1,3-propanediol solution was transferred to the feed system of a wiped film still. The feed reservoir was heated to 60° C. using a circulating hot water bath. The wiped film still was evacuated to 0.2 mm Hg, and the wall temperature was raised to 110° C. (cold finger at 60° C.). Colorless 2-amino-1,3-propanediol distillate was collected. The final recovery of 2-amino-1,3-propanediol was 68–69 grams (0.75–0.76 moles, 99.4 percent purity).

The purified 2-amino-1,3-propanediol was transferred to a jar with stirring and seeded with crystal of 2-amino-1,3-propanediol. The solid was protected from exposure to the atmosphere.

EXAMPLE 5

80.0 grams of 2-chloro-2-nitro-1,3-propanediol was dissolved in 300 ml methanol. To a pressure vessel was added 4 gm 5% palladium on char. The vessel was purged with nitrogen and 300 ml methanol were added. In addition, 80 ml. of 29% ammonia solution was added. Heat was applied and agitation began on the pressure vessel. Hydrogen pressure was applied at 800 psi. When the temperature of the pressure vessel reached 70° C. the chloronitroalcohol was introduced by pump into the vessel over a period of 2 hours. Hydrogen pressure was maintained at 800 psi and the temperature held at 70° C. during addition. Vessel conditions were maintained for an additional 3½ hours.

Hydrogen flow was stopped, pressure released, and the contents filtered to remove the suspended catalyst. The resulting clear liquid was concentrated and 85.71% of theoretical 2-amino-2,3-propanediol hydrochloride was recovered as a white crystalline solid. Product was purified by the method in Example 4.

EXAMPLE 6

24.0 grams of 50% wet palladium on char was charged to a 2-liter autoclave and mixed with 300 ml methanol. 32 ml of 28% ammonia was added. The autoclave was purged with nitrogen. Agitation was begun, the vessel was pressurized to 80 psi with hydrogen, and heated to 55° C. 80 grams of 2-chloro-2-nitro-1,3-propanediol was mixed with 160 grams methanol. This mixture was introduced to the autoclave by means of a pressure pump over a period of 30 minutes while conditions of the vessel were maintained. Agitation, heat and hydrogen pressure were maintained for an additional 2 hours.

At the end of this time pressure was released and contents of the autoclave was filtered to remove catalyst. The resulting liquid was concentrated at 60° C., 1 mm Hg. following addition of 50 ml isobutyl alcohol and the amine product was recovered and purified as related in Examples 4 and 5.

EXAMPLE 7

The present process produces high yields of high purity product under mild reaction conditions as evidenced by the following data:

| Exp | Cat. | Cat. Amt* | P. psig | Temp. °C. | NH$_3$** | Molar Yield % | GC Purity % |
|---|---|---|---|---|---|---|---|
| 1 | Ni | 5 | 150 | 65 | 1.0 | 99 | 94 |
| 2 | Pd | 5 | 80 | 55 | 1.0 | 95 | 96 |
| 3 | Pd | 5 | 80 | 55 | 1.0 | 87 | 99.7 |

*% of chloropol present.
*equivalents of NH$_3$/mol chloropol.

EXAMPLE 8

Both catalyst concentration and amount of ammonia employed have a significant impact on yield and purity. At least about 0.2 equivalents of ammonia is necessary to good yields. The catalyst charge should be at least about 0.5 wt. % based on the starting halonitroalcohol:

| Exp | Cat. | Cat. Load* | Temp. °C. | P. PSIG | NH₃** | Molar Yield % | GC Purity % |
|---|---|---|---|---|---|---|---|
| 4 | Pd | 1.3 | 75 | 750 | 0 | 0 | — |
| 5 | Pd | 1.3 | 75 | 760 | 0.2 | 41 | 61 |
| 6 | Pd | 1.3 | 70 | 780 | 0.25 | 79 | 86 |
| 7 | Pd | 0.5 | 75 | 408 | 0.25 | 73 | 78 |
| 8 | Pd | 1.3 | 75 | 400 | 1.0 | 82 | 87 |
| 9 | Ni | 1.3 | 55 | 400 | 1.0 | 86 | 92 |
| 10 | Ni | 0.5 | 75 | 800 | 1.0 | 68 | 71 |
| 11 | Ni | 0.5 | 35 | 800 | 1.0 | 58 | 58 |
| 12 | Ni | 0.5 | 51 | 400 | 0.25 | 26 | 28 |
| 13 | Ni | 1.2 | 75 | 600 | 1.0 | 93 | 86 |
| 14 | Ni | 5.0 | 65 | 150 | 1.0 | 99 | 94 |

*% of chloropol present.
**equivalents of NH₃/ml chloropol.

What is claimed is

1. A method of preparing an amino alcohol of the formula

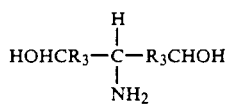

in which $R_3$ is H or lower alkyl which comprises reacting in a single step a halonitroalcohol with hydrogen in the presence of methanol, ammonia, and a hydrogenation catalyst, treating the resulting acid salt of the amino alcohol with an alkaline material, and recovering the resultant amino alcohol.

2. The method of claim 1 wherein the hydrogenation catalyst is Raney nickel or palladium on charcoal.

3. The method of claim 2 wherein the halonitroalcohol is reacted with hydrogen at a pressure above about 80 to 800 PSIG and a temperature between about 55° C. and 80° C.

4. The method of claim 3 wherein the amino alcohol-acid salt is recovered by crystallization.

5. The method of claim 4 wherein the alkaline material used to treat the amino alcohol-acid salt is sodium hydroxide.

6. The method of claim 5 wherein the sodium hydroxide is in an aqueous solution and the treatment of the amino alcohol-acid salt results in the formation of an aqueous solution of the amino alcohol and a sodium salt.

7. The method of claim 6 wherein the amino alcohol is recovered by distillation.

8. The method of claim 7 wherein the halonitroalcohol is 2-amino-2-nitro-1,3-propanediol and the amino alcohol is 2-amino-1,3-propanediol.

9. The method of claim 7 wherein the halonitroalcohol is 2-chloro-2-nitro-1,3-propanediol and the amino alcohol is 2-amino-1,3-propanediol.

* * * * *